(12) United States Patent
Clayton

(10) Patent No.: US 9,556,153 B1
(45) Date of Patent: Jan. 31, 2017

(54) JAK1 INHIBITORS

(71) Applicant: Eli Lilly and Company, Indianapolis, IN (US)

(72) Inventor: Joshua Ryan Clayton, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/221,649

(22) Filed: Jul. 28, 2016

Related U.S. Application Data

(60) Provisional application No. 62/200,684, filed on Aug. 4, 2015.

(51) Int. Cl.
*C07D 403/12* (2006.01)
*A61K 31/4184* (2006.01)

(52) U.S. Cl.
CPC ......... *C07D 403/12* (2013.01); *A61K 31/4184* (2013.01)

(58) Field of Classification Search
CPC .......................... C07D 403/12; A61K 31/4184
See application file for complete search history.

(56) References Cited

U.S. PATENT DOCUMENTS

2015/0203455 A1    7/2015  Menet et al.

*Primary Examiner* — Laura L. Stockton
(74) *Attorney, Agent, or Firm* — James B Myers

(57) ABSTRACT

The present invention relates to certain benzimidazole compounds, or pharmaceutically acceptable salts thereof, that inhibit Janus kinase 1 (JAK1), pharmaceutical compositions comprising the compounds, and methods of using the compounds to treat certain types of cancer.

28 Claims, No Drawings

JAK1 INHIBITORS

The present invention relates to certain benzimidazole compounds, or pharmaceutically acceptable salts thereof, that inhibit Janus kinase 1 (JAK1), pharmaceutical compositions comprising the compounds, and methods of using the compounds to treat certain types of cancer.

The JAK kinases are a tyrosine kinase family that regulate tyrosine phosphorylation of various effectors and initiate activation of downstream signaling pathways. JAK1 is a member of this family that mediates the activation of signal transducer and activator of transcription 3, STAT3. Persistent STAT3 activation is tumorigenic and promotes cancer cell survival and proliferation. Aberrations in STAT3 activation have been also shown to disrupt tumor immune surveillance in the tumor microenvironment. Therefore, inhibition of JAK1 can block STAT3 activation resulting in tumor growth inhibition and tumor immune surveillance. In addition, activating JAK1 mutations have been identified in both T-lineage acute lymphoblastic leukemia and Asian hepatocellular carcinoma and have been demonstrated as oncogenic. These results suggest JAK1 is a viable oncology target.

JAK2 is known to form homodimers that mediate EPO and TPO receptor-signaling to the STAT5 pathway, which regulates red blood cells and platelet production. Inhibition of JAK2 can result in anemia and thrombocytopenia. JAK1, however, does not exhibit these activities and, thus, suggests that compounds that selectively inhibit JAK1 may have a better hematotoxicity and/or immunogenicity profile than compounds that selectively inhibit JAK2 or JAK1/2 dual inhibitors.

JAK kinase inhibitor compounds are known in the literature. For example, US 2015/0203455 discloses certain benzimidazole compounds that are JAK inhibitors.

There remains a need to provide alternative JAK1 inhibitors for treatment of cancer. Also, there remains a need to provide selective JAK1 inhibitors that reduce or avoid JAK2 inhibition. Accordingly, the present invention provides certain inhibitors of JAK1 which may be useful for treating cancer. Additionally, the present invention provides certain selective JAK1 inhibitors that may reduce JAK2 inhibition.

The present invention provides a compound of Formula I:

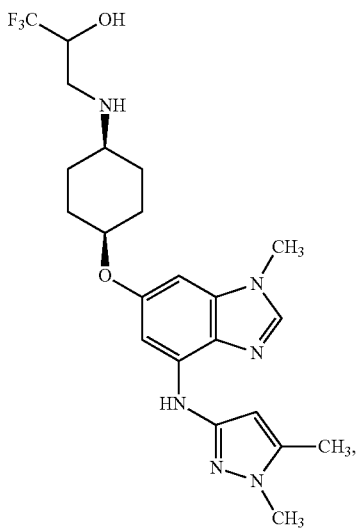

Formula I or a pharmaceutically acceptable salt thereof.

Preferably, the present invention provides a compound which is selected from the group consisting of (2S)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol:

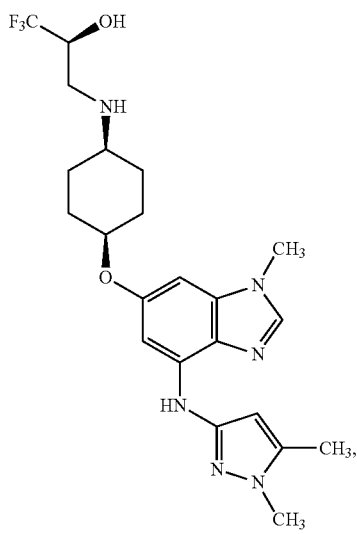 [SMILES: Cc1cc(Nc2cc(O[C@H]3CC[C@@H](NC[C@H](O)C(F)(F)F)CC3)cc3c2ncn3C)nn1C]

or a pharmaceutically acceptable salt thereof, and (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol:

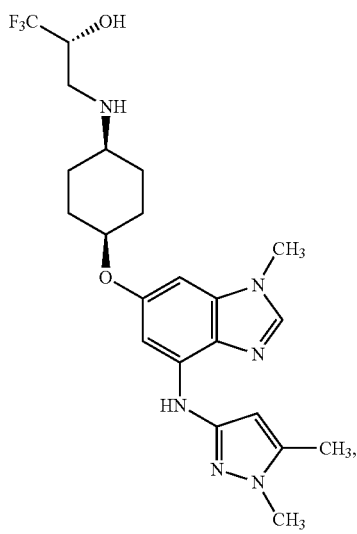 [SMILES: Cc1cc(Nc2cc(O[C@H]3CC[C@@H](NC[C@@H](O)C(F)(F)F)CC3)cc3c2ncn3C)nn1C]

or a pharmaceutically acceptable salt thereof.

Preferably, the present invention provides a compound which is (2S)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol:

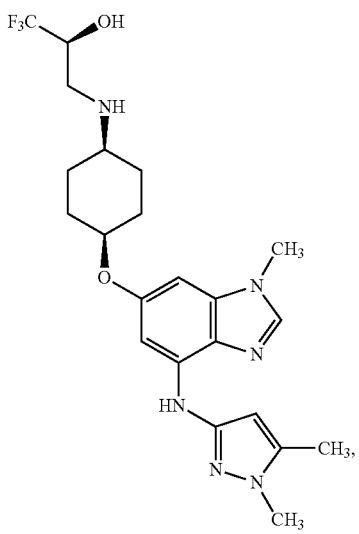 [SMILES: Cc1cc(Nc2cc(O[C@H]3CC[C@@H](NC[C@H](O)C(F)(F)F)CC3)cc3c2ncn3C)nn1C]

or a pharmaceutically acceptable salt thereof. More preferably, the present invention provides a compound which is (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol:

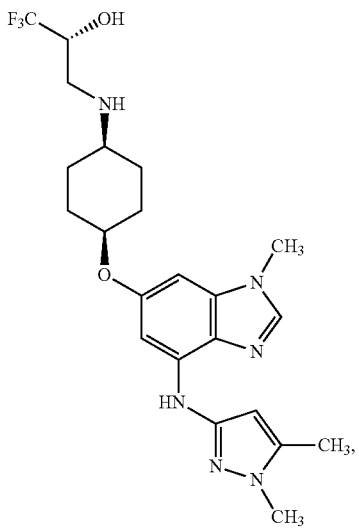

or a pharmaceutically acceptable salt thereof.

As a particular embodiment, the present invention provides a compound which is (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol.

As a particular embodiment, the present invention also provides a compound which is (2S)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol.

The present invention provides a pharmaceutical composition comprising (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, or a pharmaceutically acceptable salt thereof, and a pharmaceutically acceptable carrier, diluent, or excipient. The present invention provides a pharmaceutical composition comprising (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, and a pharmaceutically acceptable carrier, diluent, or excipient.

The present invention provides a method for treating cancer comprising administering to a patient in need thereof an effective amount of a compound of Formula I, or a pharmaceutically acceptable salt thereof. The present invention provides a method for treating cancer comprising administering to a patient in need thereof an effective amount of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, or a pharmaceutically acceptable salt thereof. The present invention provides a method for treating cancer comprising administering to a patient in need thereof an effective amount of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol.

The present invention provides a compound of Formula I, or a pharmaceutically acceptable salt thereof, for use in therapy. The present invention provides (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, or a pharmaceutically acceptable salt thereof, for use in therapy. The present invention provides (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, or a pharmaceutically acceptable salt thereof, for use in the treatment of cancer.

The present invention provides a compound of Formula I for use in therapy. The present invention also provides (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol for use in therapy. The present invention provides (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol for use in the treatment of cancer.

The present invention provides the use of a compound of Formula I, or a pharmaceutically acceptable salt thereof, in the manufacture of a medicament for the treatment of cancer. The present invention provides the use of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol, or a pharmaceutically acceptable salt thereof, in the manufacture of a medicament for the treatment of cancer. The present invention also provides the use of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol in the manufacture of a medicament for the treatment of cancer.

The present invention provides the freebase of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol in a crystalline form. The present invention also provides the freebase of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol in a crystalline form characterized by an X-ray powder diffraction pattern having characteristic peaks, in $2\theta \pm 0.2$, occurring at 19.5° in combination with one or more of the peaks selected from the group consisting of 11.9°, 15.4°, and 17.6°.

The present invention provides the dimethane sulfonic acid salt of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol in a crystalline form. The present invention also provides the dimethane sulfonic acid salt of (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol in a crystalline form characterized by an X-ray powder diffraction pattern having characteristic peaks, in 2θ±0.2°, occurring at 21.7° in combination with one or more of the peaks selected from the group consisting of 21.2°, 18.0°, and 15.7°.

Furthermore, the present invention provides preferred embodiments of the methods and uses as described herein, in which cancer is selected from the group consisting of lung cancer, including non-small cell lung cancer, small cell lung cancer, and lung adenocarcinoma, adenocarcinoma, hepatocellular carcinoma, including Asian hepatocellular carcinoma, colorectal cancer, breast cancer, lymphoma, and leukemia, including acute lymphocyte leukemia and T-lineage acute lymphoblastic leukemia. Preferred cancers are lung cancer, including non-small cell lung cancer and lung adenocarcinoma, adenocarcinoma, hepatocellular carcinoma, including Asian hepatocellular carcinoma, colorectal cancer, breast cancer, and leukemia, including acute lymphocyte leukemia. More preferred cancers are non-small cell lung cancer, lung adenocarcinoma, breast cancer, and Asian hepatocellular carcinoma.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" or "a pharmaceutically acceptable salt" refers to the relatively non-toxic, inorganic and organic salt or salts of a compound of the present invention.

"Effective amount" means the amount of a compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

A compound of the present invention is capable of reaction, for example, with a number of inorganic and organic acids to form pharmaceutically acceptable salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

A compound of the present invention is preferably formulated as a pharmaceutical composition using a pharmaceutically acceptable carrier, diluent, or excipient and administered by a variety of routes. Preferably, such compositions are for oral administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The amount of a compound of the present invention actually administered will be determined by a physician under the relevant circumstances, including the condition to be treated, the chosen route of administration, the actual compound of the present invention administered, the age, weight, and response of the individual patient, and the severity of the patient's symptoms. Dosages per day normally fall within the range of about 50 to 1000 mg per day, preferably 80 to 600 mg per day, most preferably 300 mg per day. In some instances, dosage levels below the lower limit of the aforesaid range may be more than adequate, while in other cases still larger doses may be employed. Dosage levels can be determined by one of skill in the art.

A compound of the present invention, or pharmaceutically acceptable salt thereof, may be prepared by a variety of procedures known in the art, as well as those described in the Preparations and Examples below. The specific synthetic steps for each of the routes described may be combined in different ways to prepare a compound of the invention, or pharmaceutically acceptable salt thereof.

The reagents and starting materials are generally readily available to one of ordinary skill in the art. Others may be made by standard techniques of organic and heterocyclic chemistry, techniques which are known to one of ordinary skill in the art, and the procedures described in the Examples which follow including any novel procedures. The following Preparations and Examples further illustrate the invention. Unless noted to the contrary, the compounds illustrated herein are named and numbered using IUPACNAME ACD-LABS.

Individual isomers, enantiomers, or diastereomers may be separated or resolved by one of ordinary skill in the art at any convenient point in the synthesis of compounds by methods such as selective crystallization techniques or chiral chromatography (See, e.g., Enantiomers, Racemates, and Resolutions (J. Jacques, et al., John Wiley and Sons, Inc., 1981)).

The skilled artisan will appreciate a compound of the present invention contains at least one chiral center. The present invention contemplates all individual enantiomers or diastereomers, as well as mixtures of the enantiomers and diastereomers of said compounds including racemates. It is preferred that a compound of the present invention exists as a single enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques.

A compound of the present invention can be prepared according to synthetic methods well known and appreciated in the art. Suitable reaction conditions for the steps of these reactions are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce a compound of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

As used herein, the following terms have the meanings indicated: "ATP" refers to adenosine 5'-triphosphate; "BSA" refers to bovine serum albumin; "DMSO" refers to dimethyl sulfoxide; "EDTA" refers to ethylenediaminetetraacetic acid; "EGTA" refers to ethylene glycol tetraacetic acid; "FBS" refers to fetal bovine serum; "GFP" refers to green fluorescent protein; "HEPES" refers to 4-(2-hydroxyethyl)piperazine-1-ethanesulfonic acid; "HWB" refers to human whole blood; "IC$_{50}$" refers to the concentration of compound that reduces a given response (ligand binding or enzyme response) by 50%; "IC$_{50}$ relative" refers to the relative concentration giving half the compound's maximum response; "IVTI" refers to in vivo target inhibition; "JAK" refers to Janus kinase; "MS" refers to mass spectroscopy; "NMR" refers to nuclear magnetic resonance; "NSCLC" refers to non-small cell lung cancer; "PBS" refers to phosphate buffered saline; "RNase" refers to ribonuclease; "RT" refers to room temperature; "SCLC" refers to small cell lung cancer; "STAT" refers to signal transducers and activators of transcription; "TED" refers to threshold effective dose; "TR-FRET" refers to time resolved fluorescence resonance energy transfer.

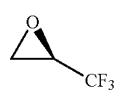

Preparation 1
(2R)-2-(Trifluoromethyl)oxirane

Add acetic acid (0.89 mL, 0.052 eq) to a solution of (1S,2S)-(+)-1,2-cyclohexanediamino-N,N'-bis(3,5-di-t-butylsalicylidene)cobalt (II) (0.90 g, 0.0050 eq) in toluene (16.65 mL). Stir at room temperature for 30 minutes. Remove the solvent in vacuo. Add toluene (20 mL) and concentrate in vacuo. Cool to 0° C. and add 2-(trifluoromethyl)oxirane (37.00 g, 330 mmol; 80.0% ee, (2R) is the major enantiomer). Stir for five minutes and add water (0.80 mL, 0.15 eq) dropwise. Allow to slowly warm to room temperature and stir overnight. Vacuum distill at room temperature, collecting the title compound in a cooled flask as a light yellow oil (28.10 g, 76%; 99.8% ee). $^1$H NMR (CDCl3) δ 2.92-2.94 (m, 1H), 2.98-3.01 (m, 1H), 3.41-3.46 (m, 1H).

Combine the title compound (0.13 g, 1.16 mmol) and methanol (1.3 mL). Cool to 0° C. and add triethylamine (0.17 mL, 1.10 eq) and thiophenol (0.12 mL, 1.05 eq). Stir for 30 minutes. GCMS of an aliquot shows formation of 1,1,1-trifluoro-3-phenylsulfanyl-propan-2-ol (from ring-opening of the title compound); m/z=222. Chiral LC-MS shows 99.8% ee, (2S)-1,1,1-trifluoro-3-phenylsulfanyl-propan-2-ol is the major enantiomer.

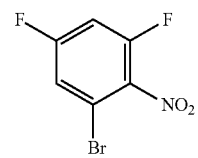

Preparation 2
1-Bromo-3,5-difluoro-2-nitrobenzene

Add nitric acid (fuming, 20 mL) dropwise to a solution of 1-bromo-3,5-difluorobenzene (35.00 mL, 304 mmol) in sulfuric acid (50 mL) at 0° C. Allow to slowly warm to room temperature and stir overnight. Pour the reaction mixture into a mix of ice and water (600 mL). Allow to slowly warm to room temperature. Add ethyl acetate (200 mL) and hexanes (100 mL). Stir until all solids dissolve. Separate the layers. Wash the organics with saturated aqueous sodium chloride, dry over anhydrous sodium sulfate, filter, and concentrate in vacuo to give the title compound as a yellow oil (57.37 g, 79%). GCMS m/z=237,239 (Br).

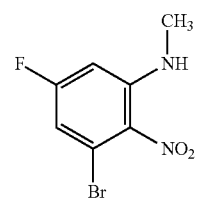

Preparation 3
3-Bromo-5-fluoro-N-methyl-2-nitroaniline

Add 2 M monomethylamine in tetrahydrofuran (92 mL, 2.00 eq) to a solution of 1-bromo-3,5-difluoro-2-nitrobenzene (21.90 g, 92 mmol) in 1,4-dioxane (92 mL). Stir at room temperature for 45 minutes. Add water and extract with ethyl acetate. Wash the organics with saturated aqueous sodium chloride, dry over anhydrous sodium sulfate, filter, and concentrate in vacuo. Purify by normal phase chromatography, eluting with a 20-40% methylene chloride in hexanes gradient, to give the title compound as an orange solid (16.95 g, 74%). MS (ES) m/z=($^{79}$Br/$^{81}$Br) 249/251 (M+H).

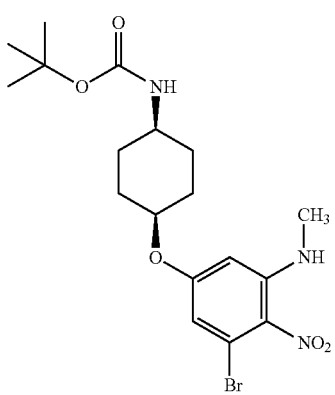

Preparation 4
tert-Butyl {cis-4-[3-bromo-5-(methylamino)-4-nitrophenoxy]cyclohexyl}carbamate Combine 3-bromo-5-fluoro-N-methyl-2-nitroaniline (75.04 g, 301 mmol), tert-butyl (cis-4-hydroxycyclohexyl)carbamate (89.52 g, 1.38 eq), and tetra(n-butyl)ammonium bisulfate (15.58 g, 0.15 eq) in dichloromethane (975 mL) and 5 M aqueous sodium hydroxide (241 mL). Stir rapidly at 37° C. under nitrogen for five days. Cool to room temperature. Dilute with dichloromethane (200 mL) and water (400 mL). Separate the layers. Extract the aqueous with dichloromethane (3×100 mL). Wash the combined organics with saturated aqueous sodium chloride, dry over anhydrous sodium sulfate, filter, and concentrate in vacuo. Purify by normal phase chromatography, eluting with a 0-40% ethyl acetate in hexanes gradient, to give the title compound as an orange solid (68.57 g, 51%). MS (ES) m/z=($^{79}$Br/$^{81}$Br) 442/444 (M−H).

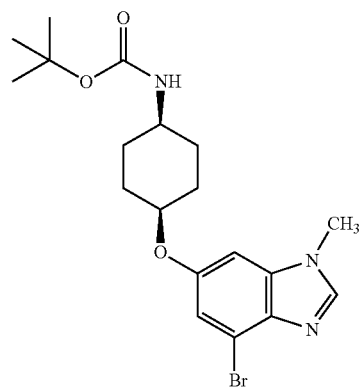

Preparation 5
tert-Butyl {cis-4-[(4-bromo-1-methyl-1H-benzimidazol-6-yl)oxy]cyclohexyl}carbamate Combine tert-butyl {cis-4-[3-bromo-5-(methylamino)-4-nitrophenoxy]cyclohexyl}carbamate (76.92 g, 173 mmol) and platinum 5% on carbon (sulfided, 3.85 g) in tetrahydrofuran (923 mL) in a Parr reactor. Stir at room temperature under 414 kPa hydrogen for three days. Filter through diatomaceous earth. Wash with tetrahydrofuran. Add trimethylorthoformate (165 mL, 8.70 eq) to the combined tetrahydrofuran filtrates. Stir for 22 hours at 63° C. Concentrate the majority of the reaction mixture in vacuo. Dilute with water (400 mL) and ethyl acetate (400 mL). Basify with aqueous sodium carbonate to adjust pH to 9. Separate the layers. Extract the aqueous with ethyl acetate (2×200 mL). Dry the combined organics over anhydrous sodium sulfate, filter, and concentrate in vacuo. Dilute with methyl tert-butyl ether (400 mL) and sonicate for 30 minutes. Filter, wash with methyl tert-butyl ether, and dry under vacuum to give the title compound as a light brown solid (52.02 g, 71%). MS (ES) m/z=($^{79}$Br/$^{81}$Br) 424/426 (M+H).

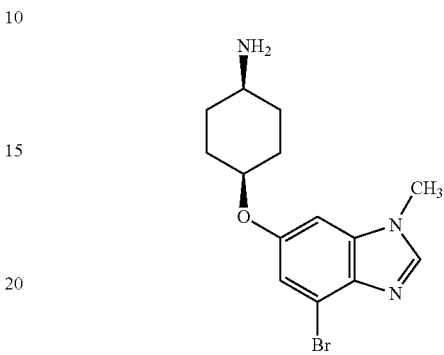

Preparation 6
cis-4-[(4-Bromo-1-methyl-1H-benzimidazol-6-yl)oxy]cyclohexanamine

Add trifluoroacetic acid (666 mL) slowly via addition funnel to a solution of tert-butyl {cis-4-[(4-bromo-1-methyl-1H-benzimidazol-6-yl)oxy]cyclohexyl}carbamate (222 g, 497 mmol) in dichloromethane (1110 mL) at 0° C. Allow to slowly warm to room temperature and stir overnight. Concentrate the reaction mixture in vacuo. Add water (250 mL) and basify with 50% aqueous sodium hydroxide to adjust pH to 10. Add water (250 mL). Extract with 20% methanol in dichloromethane (1500 mL, then 500 mL, then 250 mL). Wash the combined organics with 2 M aqueous sodium hydroxide, dry over anhydrous magnesium sulfate, filter, and concentrate to give the title compound as a brown solid (155 g, 91%). MS (ES) m/z=($^{79}$Br/$^{81}$Br) 324/326 (M+H).

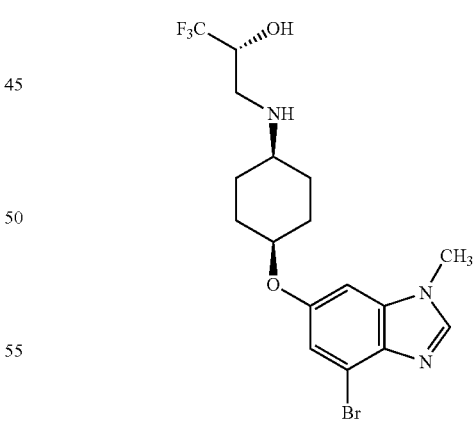

Preparation 7
(2R)-3-({cis-4-[(4-Bromo-1-methyl-1H-benzimidazol-6-yl)oxy]cyclohexyl}amino)-1,1,1-trifluoropropan-2-ol Add (2R)-2-(trifluoromethyl)oxirane (73.29 g, 1.50 eq) to a solution of cis-4-[(4-bromo-1-methyl-1H-benzimidazol-6-yl)oxy]cyclohexanamine (150.4 g, 436 mmol) in methanol (1053 mL). Stir at room temperature overnight. Concentrate the reaction mixture in vacuo. Purify by normal phase chromatography, eluting with a 0-10% ethanol in dichloromethane gradient, to give the title compound as an off-white solid (98.10 g, 52%). MS (ES) m/z=($^{79}$Br/$^{81}$Br) 436/438 (M+H).

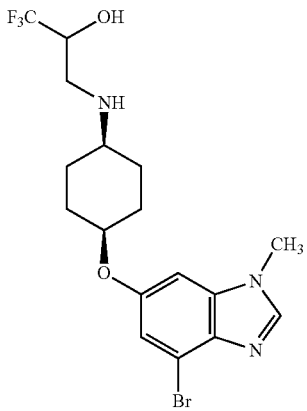

Preparation 8
3-({cis-4-[(4-Bromo-1-methyl-1H-benzimidazol-6-yl)oxy]cyclohexyl}amino)-1,1,1-trifluoropropan-2-ol Add 2-(trifluoromethyl)oxirane (2.13 mL, 1.02 eq; 80.0% ee, (2R) is the major enantiomer) to a solution of cis-4-[(4-bromo-1-methyl-1H-benzimidazol-6-yl)oxy]cyclohexanamine (7.90 g, 24.37 mmol) in isopropanol (130 mL). Heat at 70° C. overnight. Concentrate the reaction mixture in vacuo. Purify by normal phase chromatography, eluting with a stepwise gradient from 100% ethyl acetate to 2.5% to 5% to 7.5% to 10% methanol in ethyl acetate, to give the title compound (7.86 g, 74%). MS (ES) m/z=($^{79}$Br/$^{81}$Br) 436/438 (M+H).

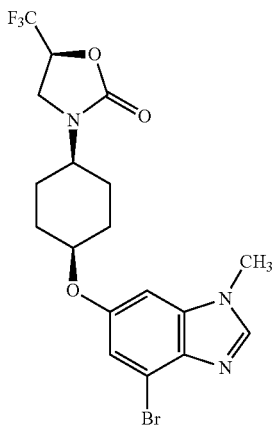

Preparation 9
(5S)-3-{cis-4-[(4-Bromo-1-methyl-1H-benzimidazol-6-yl)oxy]cyclohexyl}-5-(trifluormethyl)-1,3-oxazolidin-2-one Combine 3-({cis-4-[(4-bromo-1-methyl-1H-benzimidazol-6-yl)oxy]cyclohexyl}amino)-1,1,1-trifluoropropan-2-ol (3.34 g, 7.66 mmol; 80.0% ee, (2R) is the major enantiomer), 1,1'-carbonyldiimidazole (2.48 g, 2.00 eq), and 4-dimethylaminopyridine (0.094 g, 0.10 eq) in dichloromethane (38.3 mL). Stir at room temperature under nitrogen overnight. Concentrate the reaction mixture in vacuo. Purify by normal phase chromatography, eluting with a 0-5% methanol in dichloromethane gradient, to give 3-{cis-4-[(4-bromo-1-methyl-1H-benzimidazol-6-yl)oxy]cyclohexyl}-5-(trifluoromethyl)-1,3-oxazolidin-2-one (3.28 g; 80.0% ee, (5R) is the major enantiomer).

Separate the above with the following chiral chromatography conditions to give the title compound (0.32 g, 9%). MS (ES) m/z=($^{79}$Br/$^{81}$Br) 462/464 (M+H): Enantiomer 1, >99% ee, 75%/25% CO$_2$/MeOH, 5 mL/min, 4.6×150 mm, Chiralpak AD-H.

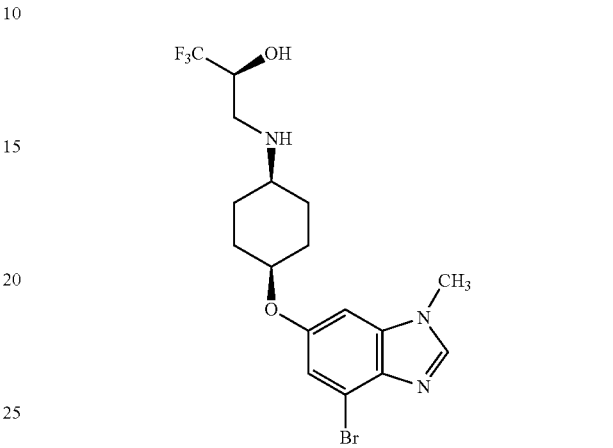

Preparation 10
(2S)-3-({cis-4-[(4-Bromo-1-methyl-1H-benzimidazol-6-yl)oxy]cyclohexyl}amino)-1,1,1-trifluoropropan-2-ol Combine (5S)-3-{cis-4-[(4-bromo-1-methyl-1H-benzimidazol-6-yl)oxy]cyclohexyl}-5-(trifluoromethyl)-1,3-oxazolidin-2-one (0.32 g, 0.69 mmol) and potassium trimethylsilanolate (0.36 g, 4.00 eq) in tetrahydrofuran (7 mL). Stir at room temperature under nitrogen for six days. Dilute with water. Filter, wash with water, and dry under vacuum to give the title compound as a white solid (0.22 g, 73%). MS (ES) m/z=($^{79}$Br/$^{81}$Br) 436/438 (M+H).

Example 1

(2R)-3-{[cis-4-({4-[(1,5-Dimethyl-1H-pyrazol-3-yl)amino]-1-methyl-1H-benzimidazol-6-yl}oxy)cyclohexyl]amino}-1,1,1-trifluoropropan-2-ol

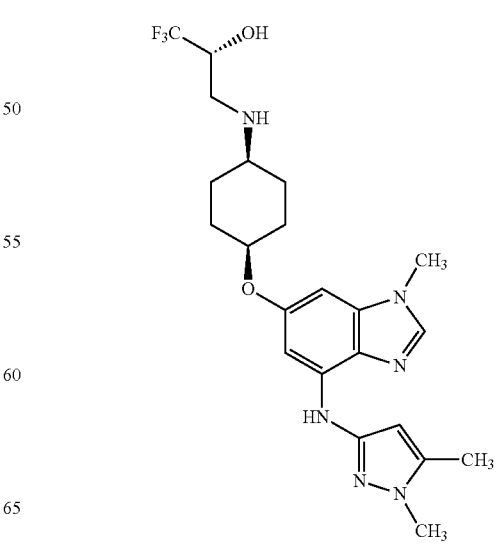

Combine (2R)-3-({cis-4-[(4-bromo-1-methyl-1H-benzimidazol-6-yl)oxy]cyclohexyl}amino)-1,1,1-trifluoropropan-2-ol (0.20 g, 0.46 mmol), 1,5-dimethylpyrazol-3-amine (0.056 g, 1.1 eq), potassium carbonate (0.158 g, 2.5 eq), 2-(di-tert-butylphosphino)-2',4',6'-triisopropyl-3,6-dimethoxy-1,1'-biphenyl (0.046 g, 0.20 eq), tris(dibenzylideneacetone)dipalladium(0) (0.042 g, 0.10 eq), and acetic acid (0.01 mL) in tert-butyl alcohol (5 mL). Seal with a crimp cap. Heat in a microwave reactor at 120° C. for 45 minutes. Concentrate the reaction mixture in vacuo. Purify by normal phase chromatography, eluting with a stepwise gradient from 100% ethyl acetate to 1% to 2.5% to 5% methanol in ethyl acetate, to give the title compound (0.071 g, 33%). MS (ES) m/z=467 (M+H).

Alternate Example 1

(2R)-3-{[cis-4-({4-[(1,5-Dimethyl-1H-pyrazol-3-yl)amino]-1-methyl-1H-benzimidazol-6-yl}oxy)cyclohexyl]amino}-1,1,1-trifluoropropan-2-ol

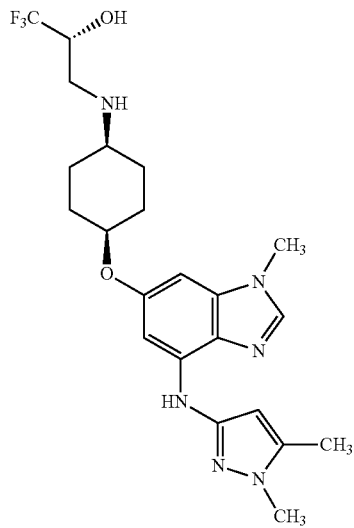 [SMILES: Cc1cc(Nc2cc(O[C@H]3CC[C@@H](NC[C@@H](O)C(F)(F)F)CC3)cc3c2ncn3C)nn1C]

Combine (2R)-3-({cis-4-[(4-bromo-1-methyl-1H-benzimidazol-6-yl)oxy]cyclohexyl}amino)-1,1,1-trifluoropropan-2-ol (50 g, 115 mmol), 1,5-dimethylpyrazol-3-amine (18.25 g, 1.43 eq), and potassium carbonate (50 g, 3.16 eq) in 2-methylbutan-2-ol (400 mL). Stir and degas with a bubbling nitrogen line for 15 minutes. Add 2-(dicyclohexylphosphino)3,6-dimethoxy-2',4',6'-triisopropyl-1,1'biphenyl (2.20 g, 0.034 eq) and tris(dibenzylideneacetone)dipalladium(0) (1.60 g, 0.015 eq). Stir and degas with a bubbling nitrogen line for five minutes. Add acetic acid (3 mL). Heat at reflux under nitrogen for twenty hours. Add 2-(dicyclohexylphosphino)3,6-dimethoxy-2',4',6'-triisopropyl-1,1'-biphenyl (1.10 g, 0.017 eq) and tris(dibenzylideneacetone)dipalladium(0) (0.80 g, 0.0075 eq). Heat at reflux under nitrogen for three hours. Concentrate the reaction mixture in vacuo. Dilute with water (500 mL). Acidify with 35% aqueous hydrochloric acid to adjust pH to 1. Add ethyl acetate (100 mL) and stir for five minutes. Treat the stirring mixture with activated charcoal (5 g) and filter through diatomaceous earth. Separate the layers and discard the organics. Basify the aqueous layer with 30% w/w aqueous ammonium hydroxide to adjust pH to 10. Filter to obtain a solid. Purify by normal phase chromatography, eluting with 10% 2 M ammonia/methanol in dichloromethane, to give the title compound (52 g, 95%). MS (ES) m/z=467 (M+H).

Second Alternate Example 1

(2R)-3-{[cis-4-({4-[(1,5-Dimethyl-1H-pyrazol-3-yl)amino]-1-methyl-1H-benzimidazol-6-yl}oxy)cyclohexyl]amino}-1,1,1-trifluoropropan-2-ol, Crystalline Form I A: Dissolve a portion of the normal phase chromatography product of Alternate Example 1 (1.60 g) in 9:1 acetone:water (45 mL). Stir at room temperature for 15 minutes and add SiliaBond® DMT (0.42 g). Filter after five hours at room temperature. Concentrate the filtrate to remove all acetone, then dilute with water (10 mL). Filter and dry under vacuum to give crystalline material (1.37 g). MS (ES) m/z=467 (M+H).

B: Slurry the normal phase chromatography product of Alternate Example 1 (47.0 g) in isopropanol (1.15 L). Heat the mixture to reflux to obtain a solution. Add glassy carbon (6 g). After one hour at reflux, filter through diatomaceous earth. Wash with isopropanol (50 mL) and seed the filtrate with crystalline material from Subsection A as provided directly above (0.20 g, portionwise). Stir and allow to cool to room temperature over two hours. Filter and dry under vacuum to give crystalline material (37.8 g). MS (ES) m/z=467 (M+H).

Example 2

(2S)-3-{[cis-4-({4-[(1,5-Dimethyl-1H-pyrazol-3-yl)amino]-1-methyl-1H-benzimidazol-6-yl}oxy)cyclohexyl]amino}-1,1,1-trifluoropropan-2-ol

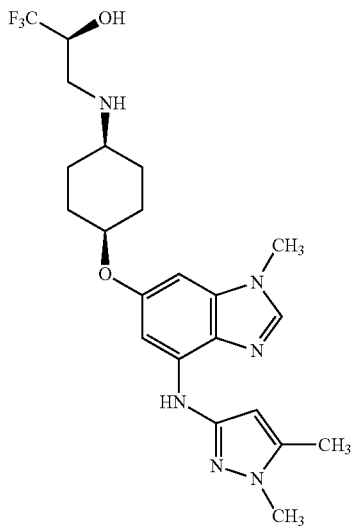

Combine (2S)-3-({cis-4-[(4-Bromo-1-methyl-1H-benzimidazol-6-yl)oxy]cyclohexyl}amino)-1,1,1-trifluoropropan-2-ol (0.077 g, 0.18 mmol), 1,5-dimethylpyrazol-3-amine (0.030 g, 1.45 eq), potassium carbonate (0.060 g, 2.46 eq), 2-(di-tert-butylphosphino)-2',4',6'-triisopropyl-3,6-dimethoxy-1,1'-biphenyl (0.022 g, 0.25 eq), tris(dibenzylideneacetone)dipalladium(0) (0.0080 g, 0.050 eq), and acetic acid (0.01 mL) in tert-butyl alcohol (2.5 mL). Seal with a crimp cap. Heat at 95° C. overnight. Dilute with ethyl acetate and filter through diatomaceous earth. Concentrate the filtrate in vacuo. Purify by normal phase chromatography, eluting with a 5-100% B gradient (A: dichloromethane; B: 15% 0.75 M ammoniated methanol in dichloromethane). Further purify by reverse phase chromatography, eluting with a 5-100% B gradient (A: 10 nM aqueous ammonium bicarbonate with 10% methanol; B: acetonitrile). Concentrate clean fractions from ethanol, then again from dichloromethane, to give the title compound (0.054 g, 65%). MS (ES) m/z=467 (M+H).

Example 3

(2R)-3-{[cis-4-({4-[(1,5-Dimethyl-1H-pyrazol-3-yl) amino]-1-methyl-1H-benzimidazol-6-yl}oxy)cyclohexyl]amino}-1,1,1-trifluoropropan-2-ol; dimethane sulfonic acid

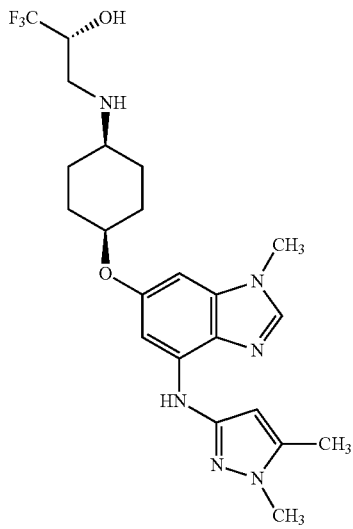 [SMILES: Cc1cc(Nc2cc(O[C@H]3CC[C@@H](NC[C@@H](O)C(F)(F)F)CC3)cc3c2ncn3C)nn1C]

Combine (2R)-3-{[cis-4-({4-[(1,5-dimethyl-1H-pyrazol-3-yl)amino]-1-methyl-1H-benzimidazol-6-yl}oxy)cyclohexyl]amino}-1,1,1-trifluoropropan-2-ol (1.00 g, 2.15 mmol) and acetone (35 mL). Heat at 51° C. and add a solution of methanesulfonic acid (0.30 mL, 2.10 eq) in acetone (5 mL) dropwise. Stir at 51° C. for one hour, and then cool to room temperature. Filter the resulting solid and dry in a vacuum oven at 70° C. overnight to give the title compound (1.25 g, 88%).

X-Ray Powder Diffraction

Obtain the XRD patterns of crystalline solids on a Bruker D4 Endeavor X-ray powder diffractometer, equipped with a CuKa source λ=1.54060 Å) and a Vantec detector, operating at 35 kV and 50 mA. Scan the sample between 4 and 40° in 2θ, with a step size of 0.009 in 2θ and a scan rate of 0.5 seconds/step, and with 0.6 mm divergence, 5.28 fixed antiscatter, and 9.5 mm detector slits. Pack the dry powder on a quartz sample holder and obtain a smooth surface using a glass slide. Collect the crystal form diffraction patterns at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2° in 2θ will take into account these potential variations without hindering the unequivocal identification of the indicated crystal form. Confirmation of a crystal form may be made based on any unique combination of distinguishing peaks (in units of ° 2θ), typically the more prominent peaks. Adjust the crystal form diffraction patterns, collected at ambient temperature and relative humidity, based on NIST 675 standard peaks at 8.853° and 26.774° 2θ.

Characterize a prepared sample of the compound of Second Alternate Example 1 by an XRD pattern using CuKa radiation as having diffraction peaks (2 θ values) as described in Table 1 below, and in particular having peaks at 19.5 in combination with one or more of the peaks selected from the group consisting of 11.9, 15.4, and 17.6; with a tolerance for the diffraction angles of 0.2°.

TABLE 1

X-ray powder diffraction peaks of Second Alternate Example 1

| Peak | Angle (°2-Theta) +/− 0.2° | Relative Intensity (% of most intense peak) |
|---|---|---|
| 1 | 6.4 | 17.0% |
| 2 | 11.9 | 46.6% |
| 3 | 14.7 | 11.7% |
| 4 | 15.4 | 41.9% |
| 5 | 16.2 | 27.5% |
| 6 | 16.9 | 24.9% |
| 7 | 17.6 | 40.1% |
| 8 | 19.5 | 100.0% |
| 9 | 20.8 | 32.1% |
| 10 | 21.5 | 19.6% |

Characterize a prepared sample of the compound of Example 3 by an XRD pattern using CuKa radiation as having diffraction peaks (2θ values) as described in Table 2 below, and in particular having peaks at 21.7 in combination with one or more of the peaks selected from the group consisting of 21.2, 18.0, and 15.7; with a tolerance for the diffraction angles of 0.2°.

TABLE 2

X-ray powder diffraction peaks of Example 3

| Peak | Angle (°2-Theta) +/− 0.2° | Relative Intensity (% of most intense peak) |
|---|---|---|
| 1 | 5.6 | 26.2% |
| 2 | 10.0 | 25.7% |
| 3 | 13.1 | 28.7% |
| 4 | 15.7 | 70.0% |
| 5 | 18.0 | 90.5% |
| 6 | 19.6 | 64.5% |
| 7 | 20.6 | 41.8% |
| 8 | 21.2 | 99.3% |
| 9 | 21.7 | 100.0% |
| 10 | 22.3 | 59.9% |

JAK1, JAK2 and JAK3 In Vitro Enzyme Assays

The JAK LanthaScreen™ Kinase Assay (Invitrogen) is used to determine the ability of test compounds to inhibit JAK1, JAK2 and JAK3 kinase activity. These are TR-FRET assay formats that use long-lifetime terbium labeled antibody as the donor species and GFP-STAT1 as the acceptor species. Use the TR-FRET ratio to monitor JAK kinase activity where an increase in phosphorylation of the GFP-STAT1 results in an increase in the TR-FRET ratio. Perform the kinase reaction using a 12.5 µl reaction volume in shallow black 384-well Proxiplate. Add reagents to obtain final reaction conditions of 50 ml HEPES pH, 1.76 mM Triton X-100, ATP (20.0 µM for JAK1 and JAK3 or 5 µM for JAK2) enzyme assays, 10.0 mM $MgCl_2$, 1 mM EGTA and 0.01% Brij-35, 0.05 mM GFP-STAT1, 14 nM JAK1 enzyme for JAK1, 1.0 nM for JAK2 or 2.5 nM for JAK3 enzyme assays, and 4% DMSO and serial dilutions of test compound (diluted 1:3 from 20,000 to 1 nM). Following ATP/GFP-STAT1 addition, centrifuge the assay plates for 1 minute at 1000 revolutions per minute (RPM). Allow the plates to incubate at RT for 60 minutes and then add 12.5 µl of a stopping buffer containing 20 mM EDTA, 2 nM Terbium-anti-phosphorylated Signal Transducers and Activators of Transcription [phosphorylation Tyrosine 701 amino acid] Antibody (Tb-anti-pSTAT1[pTyr701], 0.67 mM tris(hydroxymethyl)aminoethane hydrochloride (Trizma®) pH 7.5, 0.02% $NaN_3$ and 0.01% nonylphenylpolyethylene glycol (Nonidet® P40). Incubate at RT for 90 min and read in an EnVision plate reader with 340 nm wavelength excitation filter and emission filters of 520 nm and 495 nm wavelengths. Derive the ratio from the emission wavelength for the GFP-STAT1 which is measured at 520 nm versus the emission at 495 nm for the (Tb-anti-pSTAT1[pTyr701]. Derive the $IC_{50}$ value for each compound using percent inhibition data which is calculated from the reaction data relative to on-plate controls (active enzyme versus enzyme inhibited at 2.0 mM with tofacitinib). Use ACTIVITYBASE 4.0 to fit the percent inhibition and ten-point compound concentration data to a four-parameter logistic equation.

A compound within the scope of the invention is tested in this assay substantially as described above. The compound of Example 1 shows a JAK1 $IC_{50}$ of 4.0±0.8 nM (n=6), a JAK2 $IC_{50}$ of 557±337 nM (n=6), and a JAK3 $IC_{50}$ of 1910±786 nM (n=6). The results show that the compound of Example 1 inhibits JAK1 enzyme in vitro. These results also show that the compound of Example 1 is a more potent inhibitor of JAK1 enzyme and selective over JAK2 and JAK3 in vitro.

BaF3 Mutant JAK-1 (S729C) Clone 12 Proliferation Assay

The purpose of this assay is to determine the inhibitory activity of JAK-1 specific inhibitors using the BaF3 mutant JAK-1 (S729C) Clone 12 proliferation assay.

mtJAK1 (S729C) expressing cell line is created by transducing Ba/F3 cells (Murine pro-B-cells) with a retrovirus expressing human mtJAK1 (S729C)-pQCXIN vector DNA. Single cell cloning is performed to select Ba/F3 cells expressing highest levels of mtJAK1 (S729C) by serial dilution. BaF3 mutant JAK-1 (S729C) suspension cells are cultured and maintained in (Gibco RPMI 1640 cat# A10491-01) containing 10% Hi-FBS (Hyclone cat#10082-047), 1 µg/ml puromycin dihydrochloride (Sigma cat#9620), 1.0 mg/mL G418 sulfate (Corning ref#30-234-CI), referred to as R10+ from now on.

Proliferation assays are performed in culture medium without selection and from now on will be referred to as (R10−). Briefly, cultured cells are decanted, centrifuged and reconstituted in 10 mL of R10− and counted using a Beckman Coulter Vi-Cell. Cells are further diluted to 2e4/mL in R10− and plated in a 96 well white opaque assay plates (Costar cat#3610) at $1 \times 10^3$ cells (50 µls) per well. In corresponding 96 well polypropylene plates, test compounds are diluted in 100% DMSO followed by an additional dilution in R10− to yield a 2x test compound template. Diluted test compounds are added to the corresponding cell plate to yield a CRC from 20 µM to 0.001 µM. Minimum and maximum controls are included on each plate. Staurosporine (1 µM final) is used for the minimum control and R10− containing equivalent DMSO levels as the CRC is used as the maximum control. Plates are covered with water filled Microcline evaporation lids (cat# LLS-0310) and incubated at 37° C. in 5% $CO_2$ for 3 days. Following the 3 day incubation, plates are removed from the incubator and allowed to cool to ambient temperature. Once cooled, the plates are developed by adding 100 µL of Cell Titer Glo (Promega cat# G7571), mixing 2 minutes on a plate mixer and incubating an additional 10 mins at room temperature. Luminescence is then read on a Perkin Elmer Victor2 using a preset program for luminescence at 0.1 second. $IC_{50}$ curves are generated using an internal STAT5 TMAG program and GraphPad Prism version 4.03.

A compound within the scope of the invention is tested in this assay substantially as described above. The compound of Example 1 shows an $IC_{50}$ of 956 nM±217 nM (n=4). The result shows that the compound of Example 1 is active against mtJAK1 (S729C) expressing in Ba/F3 cells.

AlphaScreen SureFire Protocol
p-STAT5-(p-Tyr705)-IL6-TF-1-JAK1 Cell-Based Assay

The JAK1 cell based assay described below is used to determine the JAK1 cellular potency of test compounds.

Cell Preparation:
Starve TF-1 cells in DMEM medium with 0.5% 26400 (FBS) and 1x Pen/Strep at 37° C. Plate 100K cells per well in BD 96 well black plates with clear bottoms. Maintain the plates at RT for 30-60 minutes before incubating overnight at 37° C. and 5% $CO_2$. Count cells using Vi-Cell counter, using a cell suspension at 100 cells/mL and plated 100 µL/well in Beckman Dickinson Biocoat plates (Catalog #354640).

Test Compound Preparation and Treatment:
Prepare compounds at 1:3 serial dilutions in DMSO and further dilute into the medium. Test compounds in a range of 10 point concentrations from 20,000 to 1 nM. Add diluted compound to corresponding cell plates. Incubate the plates at 37° C. for 20 min. Add IL6 solution at the final concentration 30 ng/mL to corresponding cell plates and continue to incubate at 37° C. for 30 min. Remove media and add 50 µL 1x lysis buffer to each well.

pSTAT3 Detection:
Perform the following steps sequentially: make acceptor mix (activation buffer/reaction buffer/acceptor beads); transfer 4 µL lysate from 96 well plates to 384 well-Proxiplates; add 5 µL acceptor mix to 384 proxiplate plate(s) and seal plates with aluminum seal; shake 1-2 minutes on plate shaker; incubate plate at RT for 2 hr with gentle shaking; make donor mix (donor beads in dilution buffer); add 2 µL donor mix to assay plates; seal plates with aluminum seal; shake 1-2 minutes on plate shaker; incubate at RT for 2 hr with gentle shaking; read plate with Envision; protocol AlphaScreen Surefire 384.

A compound within the scope of the invention is tested in this assay substantially as described above. The compound of Example 1 shows an $IC_{50}$ of 87 nM±75 (n=10). This result shows that the compound of Example 1 inhibits JAK1 enzyme in a cell based assay.

Phospho-STAT3 (Tyr705) ACUMEN Protocol—H1975-JAK1 Cell-Based Assay

An H1975-JAK1 cellular assay is used to confirm the potency of test compounds in NSCLC cells in which the STAT3 pathway is activated by autocrine IL-6 loop.

Cell Preparation:

Perform the following steps sequentially: examine cells under the microscope; aspirate media off the cells with a sterile vacuum-driven pipette; wash cells with approximately 5 mL PBS; aspirate off PBS with a sterile vacuum-driven pipette; add 5 mL of 0.25% Trypsin-EDTA to 150 cm² flask; gently rock flask to cover cells with trypsin and let sit in hood for 3 minutes or place flask in incubator for 3 minutes to loosen cells from flask; agitate flask a few times to ensure cells are loose; add 10 mL of growth media to flask, gently dispense suspension over the cell growth side of the flask and pipette up and down to triturate cells; spin (1300 rpm 5 min), resuspend in 10 mL of growth media; strain through a cell strainer (BD Falcon 352350, 70 μm cell strainer); collect the cells in a sterile 50 mL sterile conical tube; count cells using Vi-Cell counter (0.5 mL cells).

Day 1: Plate 30000 cells per well in BD 96 well black plates with clear bottoms. Count cells using Vi-Cell counter, use a cell suspension at 300000 cells/mL and plated 100 μL/well in Beckman Dickinson Biocoat plates Catalog #354640. Maintain the plates RT for 30-60 minutes before putting them into the incubator. Then incubate overnight at 37° C. and 5% $CO_2$.

Compound Preparation and Treatment:

Prepare a deep well plate containing 1 mL media without FBS with 0.6% DMSO, then add 2 μL of compound (10 mM DMSO solution), making a 20 μM stock plate. Perform 1:3 serial dilutions of the compounds in media without FBS with 0.6% DMSO in the dilution plates. Test compounds in a range of 10 point concentrations from 20 μM to 1 nM. Remove media from the assay plates with cells. Transfer 100 μL of compounds from the dilution plate to the assay plates (Beckman Dickinson Biocoat plates Catalog #356440) containing the cell attached with 100 μL media, and use TEMO program: SAMPLE TRANSFER CELL BASED ASSAY from 3797 slow dispense.gem. Then incubate the cells for 4 hr at 37° C.

pSTAT3 Detection:

On Day 1, perform the following steps sequentially: remove media; add 100 μL of 3.7% para-formaldehyde; incubate for 30 minutes in the dark; wash with 100 μL PBS; add 100 μL cold methanol; incubate 15 minutes in the dark; wash 2 times with 100 μL PBS; add 100 μL blocking solution (1% BSA in PBS); incubate for 30 minutes in the dark; add 50 μL primary antibody pSTAT3 1:500 (in blocking solution: 1% BSA; Mouse Anti-phospho-STAT3 (Tyr705)); seal plates with aluminum foil and incubate at 4° C. with gentle shaking overnight.

On Day 2, perform the following steps sequentially: wash 2 times with 100 μL PBS; add 50 μL of secondary antibody (1:1000; Ab2° goat anti-mouse IgG); incubate for 1 hour at RT in the dark; wash 2 times with 100 μL PBS; add 100 μL of Propidium Iodide (1:1000 in PBS from commercial solution) containing RNAse (50 μg/mL in PBS); seal plates with transparent film and incubate at RT for 2 hours before reading; read on Acumen Explorer (set parameter based on positive and negative well). Laser (Scan 1) 488 nm.

Data Processing:

Process data through Activity Base and analyze using a 4-parameter nonlinear logistic equation (four-parameter logistic concentration-response curve):

$$Y=bot+[(top-bot)/1+(x/IC50)slope]$$

where Y=% inhibition, X=concentration yielding y % inhibition, Bottom=minimum value of y attained by curve, Top=maximum value of y attained by curve and Slope=steepness of curve at IC50.

$$\% \, Inh=[(\text{median Max}-x/\text{median Max}-\text{median Min})]\cdot 100$$

A compound within the scope of the invention is tested in this assay substantially as described above. The compound of Example 1 shows an $IC_{50}$ of 297 nM (n=1) The result shows that the compound of Example 1 is active against JAK1 in NSCLC cells in which the STAT3 pathway is activated by autocrine IL-6 loop.

AlphaScreen SureFire Protocol p-STAT5 (p-Tyr694/699)-EPO-JAK2 Cell-Based Assay The fold selectivity of test compounds for JAK1 over JAK2 is determined by a cellular assay, in which EPO is used to activate JAK2-STAT5 pathway, and pSTAT5 is used as the readout.

Cell Preparation:

Starve UT-7 cells overnight in DMEM medium with 0.5% 1600 (FBS) and 1× Pen/Strep at 37° C. (without GM-CSF). Plate 50000 cells per well in BD 96 well black plates with clear bottoms (in medium without FBS and GM-CSF). Maintain the plates at RT for 30-60 minutes before incubating overnight at 37° C. and 5% $CO_2$. Count cells using Vi-Cell counter, use a cell suspension at 500000 cells/mL and plated 100 μL/well in Beckman Dickinson Biocoat plates Catalog #354640.

Compound Dilution and Treatment:

Test compounds in a range of 10 point concentrations from 20,000 to 1 nM. Prepare compounds at 1:3 serial dilutions in DMSO and further dilute into the medium. Add diluted compound to corresponding cell plates and incubate at 37° C. for 20 min, then add 20 μL EPO (295 ng/mL. Final concentration 45 ng/mL) to corresponding cell plates, continue to incubate at 37° C. for 30 min.

Lyse Cells:

Dump media (carefully) and add 50 μL 1× lysis buffer to each well (freeze lysate ON). (lysis buffer: 5×; diluted in water to a final concentration of 1×).

p-STAT5 Detection:

Follow the following steps sequentially: make acceptor mix (activation buffer/reaction buffer/acceptor beads); transfer 4 μL lysate from 96 well plates to 384 well-Proxiplate; add 5 μL acceptor mix to 384 proxiplate plate(s) with multidrop combi; seal plates with aluminum seal; shake 1-2 minutes on plate shaker; incubate plate at RT for 2 hr with gentle shaking; make donor mix (donor beads in dilution buffer); add 2 μl donor mix to assay plates with multidrop combi; seal plates with aluminum seal; shake 1-2 minutes on plate shaker; incubate at RT for 2 hr with gentle shaking; read plate with Envision; protocol AlphaScreen Surefire 384.

A compound within the scope of the invention is tested in this assay substantially as described above. The compound of Example 1 exhibited an $IC_{50}$ of 11.8 μM±5.4 (n=5) The result shows that the compound of Example 1 is selective for JAK1 over JAK2 in a cellular assay, in which EPO is used to activate JAK2-STAT5 pathway Human Whole Blood Assays: Determination of pSTAT3 (JAK1) and pSTAT5 (JAK2) in Lymphocytes and Monocytes Human whole blood (HWB) assays were developed and validated to determine the JAK1 and JAK2 selectivity of test compounds.

Dilute the test compounds, 10 points, (1:3) in DMSO 100% and a step down in PBS+0.1% BSA. Use tofacitinib as a reference compound in each plate, as well as a maximum signal (stimulated wells) and a minimum signal (no stimulated wells) in order to normalize data. Obtain a pool of HWB from 4 different healthy donors. Plate the blood in a 96 well plate using a Tecan Evo 96w and incubate with test compounds for 1 h at RT. After this time of incubation, stimulate HWB with both IL6 (206-IL, R&D System) and GM-CSF (PHC2015, Life Technologies) for 15 more minutes. Add a viability dye (65-0865, eBiosicience) (1:1000) using a Tecan Evo 96w (5× mix).

The final concentrations in the assay are the following: 100 µM for compounds, 50 µM for tofacitinib, 0.1 µg/mL IL6, 0.038 µg/mL GM-CSF and 1% DMSO. Lyse and fix HWB using a Lyse/fix buffer (558049, Becton Dickinson) by adding 900 µL of lysis buffer using Tecan Evo 96w (mix 10× high speed). Incubate HWB in bath at 37° C. for 10 minutes. Centrifuge HWB at 500 G, 8 min and discard supernatant. Add cold methanol using a Tecan Exo 96w in order to permeabilize cells. Incubate blood cells in ice during 30 min. After this, wash cells 2× using Staining buffer (554656, Becton Dickinson), spin at 3000 rpm, 2 min, discard supernatant, and add the following antibodies: Anti-Human CD4 PE, 1:100 (12-0048, eBioscience), Anti-Human CD33 eFluor® 450, 1:50 (48-0337, eBioscience), Phospho-STAT5 (Tyr694) (C71E5) Rabbit mAb, 1:100 (Alexa Fluor® 488 Conjugate)(3939, Cell Signalling) and Phospho-STAT3 (Tyr705) (D3A7) XP™ Rabbit mAb 1:200, (Alexa Fluor® 647 Conjugate)(4324, Cell Signalling). Incubate the antibodies for 1 h in dark at RT, then wash cells 2× and read on Cytometer Macsquant (Miltenyi Biotec). Gate the data on CD4+(lymphocytes) and CD4Low CD33Hi (monocytes), to measure the fluorescence from cells expressing pSTAT3 and pSTAT5 respectively. Analyze the data using FlowJo v_10 and the normalize the median of fluorescence versus maximum and minimum signal to determine the $IC_{50}$s. Use Graph Pad prism 5 to represent the dose response curves.

A compound within the scope of the invention is tested in this assay substantially as described above. The compound of Example 1 shows an $IC_{50}$ of 2.40±0.64 µM (n=3) for JAK1 and an $IC_{50}$ of 13.0±3.2 µM (n=3) for JAK2. The results demonstrate that the compound of Example 1 shows approximately 5× more potency for JAK1 over JAK2 in a human whole blood assay.

pSTAT3 Mouse IVTI (JAK1) Assay

The purpose of this assay is to measure the ability of test compounds to inhibit the phosphorylation of STAT3 (STAT3 activation) in the H1975 xenograft mouse model. Grow H1975 cells according to ATCC specifications at the lowest possible passage number available. Culture and maintain cells in RPMI-1640 supplemented with 10% FBS and incubated at 37° C. in 5% $CO_2$. Harvest cells by standard techniques and mix with BD Biosciences basement membrane matrix (MATRIGEL®) to cell suspension to achieve a 1:1 cell/matrix ratio yielding an inoculation volume of 0.2 mL cell/matrix suspension containing 5e6 cells. Keep cell suspensions on ice throughout the inoculation procedure and start implantations within one hour after cell culture harvest. Administer all implantations subcutaneously in the right rear flank of female Athymic Nude mice obtained from Harlan. Feed all mice Harlan Teklad #2920X ad libitum and provide water by gel packs. Allow the implanted tumor cells to grow as a solid tumor and measure twice a week along with body weight, beginning 5-9 days post implant. Determine tumor volumes using the calculation: 0.536*L*W^2. After tumor volume reaches approximately 200-250 $mm^3$, randomize animals using the multi task block randomization tool and place into a vehicle group containing 6-10 animals and multiple treatment groups containing 6 animals each. Formulate the test compounds in 1% HEC vehicle containing 0.25% Tween 80 and 0.05% antifoam with 1.1 molar equivalent of methanesulfonic acid to form an in situ salt. Do not add acid to the vehicle control group. Calculate doses based on the most recent group mean body weight. Administer compounds by oral gavage for both the dose response and time course studies. Dose response studies are a single dose administered for 2 hours prior to tumor removal, processing and freezing. Time course studies are a single dose administered at the $TED_{70}$ determined from the dose response study.

Tumor Tissue Processing:

Harvest and cut tumors to yield approximately 150-250 $mm^3$ size fragments and immediately drop into a 12×75 mm tube containing 1 mL of ice cold MSD Tris Lysis buffer (Meso Scale Discovery cat# R60TX-2) and 1×HALT (Thermo Scientific product #1861281). Homogenize samples for approximately 15 seconds using a disposable hard tissue omni tip homogenizer probe (Omni International cat#3_750H) and allow to sit on wet ice for an additional 15-25 minutes prior to transferring to a −60° C. freezer overnight. Remove samples from the freezer and allow to sit at RT to initiate thawing. Once samples begin to thaw, transfer to wet ice and continue thawing. After thawing is completed, vortex samples and transfer to a 1.8 mL microfuge tube. Centrifuge lysates at 14,000×g for 30-60 minutes at 4° C. Transfer lysates (200 µL) to a 96 well polypropylene plate (Costar cat#3879). Determine protein concentrations using the Pierce BCA Protein Assay kit (cat#23225) as indicated below. Briefly, a standard curve is generated using a BSA standard diluted in RIPA lysis buffer containing 1×HALT to yield a working range of 2,000 µg/mL to 25 µg/mL. All lysates are diluted 1:10 in RIPA lysis buffer containing 1×HALT. Pipette 25 µL of the standards and samples into a 96 well plate (Falcon cat#353072) and add 200 µL of the working reagent to each well and mix plate thoroughly on a plate shaker for 30 seconds. Cover plate and incubate at 37° C. for 30 minutes. Cool plate to RT and measure absorbance at or near 562 nm on Molecular Devices Spectra Max. Protein concentrations for each sample are determined using SoftMax Pro 6.3 software program. After tumor samples are quantitated, freeze lysates at −80° C. in the 96 well polypropylene plate and assay at a later date.

pSTAT3 Measurement:

Perform the pSTAT3 (Tyr705) assay as follows. The MSD pSTAT3 assay kit is from Meso Scale Discovery (Cat# K150DID-2). The 100×HALT protease and phosphatase inhibitor may be substituted for the kit phosphatase and protease inhibitors based on ease of use and performance Prepare the MSD Tris Lysis buffer by adding 100×HALT protease and phosphatase inhibitor to a 1× final concentration, referred to as MSD complete lysis buffer. Remove tumor samples from the −80° C. freezer and allow to sit at RT to initiate thawing. During the sample thaw, block the pSTAT3 Tyr705 capture plate (cat# K150DID-2) with 150 µL of a blocking solution for a minimum of 1 hr at RT on a plate shaker with vigorous shaking (300-1000 rpm). Seal plates with an adhesive plate seal prior to shaking. Blocking solution contains the ratio of Blocker A (cat# R93BA-4) 600 mgs: 20 mL of 1×MSD Tris wash buffer (cat# R61TX-2). Once samples begin to thaw, transfer to wet ice to continue thawing. After thawing is completed, carefully mix by pipetting up and down several times using a multichannel pipette. Normalize samples in ice cold MSD complete lysis buffer to a protein concentration of 0.4 µg/µL×100 µL. Maintain all normalized tumor samples on ice in a 96 well polypropylene plate until they are added to the pSTAT3 capture plate. After the pSTAT3 capture plate is blocked, wash 4× with 250-300 µl of 1×MSD Tris wash buffer using a Thermo Labsystems Multidrop 384 plate washer. After the final wash, tap the plate lightly to remove any remaining wash buffer. Add a total volume of 25 µL (10 µg) of normalized tumor lysate per well and incubate an additional 2-3 hours at RT on a plate shaker with vigorous shaking (300-1000 rpm). During this incubation, dilute the Sulfo-TAG anti Phospho-STAT 3 detection antibody provided in the kit in the antibody dilution buffer (1 ml of blocking solution combined with 2 mL of 1×MSD Tris wash buffer) by adding 60 µL of Sulfo-TAG anti Phospho-STAT 3 detection antibody to 2.94 mL of antibody dilution buffer. Keep this antibody solution on wet ice until needed. Following tumor lysate incubation, wash the plate 4× with 250-300 µL of 1×MSD Tris wash buffer. After the last wash, tap the plate to remove any remaining wash buffer and add 25 µL/well of the Sulfo-TAG anti Phospho-STAT 3 detection antibody. Incubate the plate an additional 1 hour at RT on a plate shaker with vigorous shaking (300-1000 rpm). During this incubation, dilute the 4×MSD Read Buffer T with surfactant (cat# R92TC-3) to 1× with deionized water and keep at RT. After the detection antibody incubation is complete, wash the plate 4× with 250-300 µL of 1×MSD Tris wash buffer. After the final wash, tap the plate lightly to remove any remaining wash buffer and add a total volume of 150 µL/well of 1×MSD Read Buffer T with surfactant. Read the plate on the Meso Quick Plex SQ 120. Analyze data as indicated below.

Percent pSTAT3 Inhibition Calculation:

Copy and paste raw plate data from the Meso Quick Plex SQ 120 directly into a Microsoft Excel version 2010 worksheet. Organize data into the appropriate format (Dose Response or Time Course), copied and pasted directly into JMP version 11 for pSTAT3 percent inhibition calculations (see formula below).

[1−(Treatment sample Signal/Mean Signal of Vehicle Control)]*100.

Determine a Oneway Anova with treatment group mean compared to vehicle control mean using Dunnett's.

TED Calculations:

Determine the $TED_{50}$ and $TEC_{50}$ values from a dose response study. The $TED_{50}$ and is the dose necessary to achieve 50% pSTAT3 inhibition and $TEC_{50}$ is the plasma concentration to achieve 50% pSTAT3 inhibition, respectively, at two hours.

A compound within the scope of the invention is tested in this assay substantially as described above. The compound of Example 1 shows a $TED_{50}$ of 35 mg/kg and a $TEC_{50}$ of 11.1 µM (n=1). These results show that the compound of Example 1 effectively inhibits JAK1-STAT3 signaling (using pSTAT3 as a readout), in vivo at 2 hours after orally dosing. These results show that the compound of Example 1 also demonstrates PK/PD correlated activity with $TEC_{50}$ pSTAT3 Rat IVTI (JAK1) Assay The purpose of this assay is to measure the ability of test compounds to inhibit the pSTAT3 expression in the H1975 xenograft rat model. Grow H1975 cells according to ATCC specifications at the lowest possible passage number available. Culture and maintain cells in RPMI-1640 supplemented with 10% FBS and incubated at 37° C. in 5% $CO_2$. Harvest cells by standard techniques and mix with BD Biosciences basement membrane matrix (MATRIGEL®) to achieve a 1:1 cell/matrix ratio yielding an inoculation volume of 0.2 mL cell/matrix suspension containing 2e6 cells. Keep cell suspensions on ice throughout the inoculation procedure and start implantations within one hour after cell culture harvest. Administer all implantations subcutaneously in the right rear flank of female NIH Nude rat obtained from Taconic. Feed all rats Harlan Teklad Global Diets #2920X ad libitum and provide water bottles. Allow the implanted tumor cells to grow as a solid tumor and measure twice a week along with body weight. Begin measuring body weight and tumor volumes 5-9 days post implant. Determine tumor volumes using the calculation: $0.536*L*W^2$. After tumor volume reaches approximately 350-400 mm$^3$, randomize animals using the multi task block randomization tool and place into a vehicle group containing 6 animals and multiple treatment groups containing 6 animals each. Formulate the compounds in 1% HEC vehicle containing 0.25% Tween 80 and 0.05% antifoam with 1.1 molar equivalent of methanesulfonic acid to form an in situ salt (1.1 mL of 1N methanesulfonic acid per mg of compound). Do not add acid to the vehicle control group. Calculate doses based on the most recent group mean body weight. Administer all compounds by oral gavage for both the dose response and time course studies. Dose response studies are a single dose administered for 2 hours prior to tumor removal, processing and freezing. Time course studies are a single dose administered at the $TED_{70}$ determined from the dose response study. Perform tumor removal, processing and freezing occurs at multiple time points outlined below.

Tumor Tissue Processing

Harvest and cut tumors to yield approximately 200-250 mm$^3$ size fragments and immediately drop into a 12×75 mm tube containing 1 mL of ice cold MSD Tris Lysis buffer (Meso Scale Discovery cat# R60TX-2) and 1×HALT (Thermo Scientific product #1861281). Homogenize samples for approximately 15 seconds using a disposable hard tissue omni tip homogenizer probe (Omni International cat#3_750H) and allow to sit on wet ice for an additional 15-25 minutes prior to transferring to a −60° C. freezer overnight. Remove samples from the freezer and allow to sit at RT to initiate thawing. Once samples begin to thaw, transfer to wet ice to continue thawing. After thawing is completed, vortex samples and transfer to a 1.8 mL microfuge tube. Centrifuge the lysates at 14,000×g for 30-60 minutes at 4° C. Transfer lysates (200 µL) to a 96 well polypropylene plate (Costar cat#3879) corresponding to the 96 well sample template design. Determine protein concentrations using the Pierce BCA Protein Assay kit (cat#23225) as indicated below. Briefly, a standard curve is generated using a BSA standard diluted in RIPA lysis buffer containing 1×HALT to yield a working range of 2,000 µg/ml to 25 µg/mL. All lysates are diluted 1:10 in RIPA lysis buffer containing 1× HALT. Pipette 25 µL of the standards and samples into a 96 well plate (Falcon cat#353072) and add 200 μL of the working reagent to each well and mix plate thoroughly on a plate shaker for 30 seconds. Cover plate and incubate at 37° C. for 30 minutes. Cool plate to RT and measure absorbance at or near 562 nm on Molecular Devices Spectra Max. Protein concentrations for each sample are determined using SoftMax Pro 6.3 software program. After tumor samples are quantitated, freeze at −80° C. in the 96 well polypropylene plate and assay at a later date.

pSTAT3 Measurement

The pSTAT3 (Tyr705) assay is performed as follows. The MSD pSTAT3 assay kit is from Meso Scale Discovery (Cat# K150DID-2). The 100×HALT protease and phosphatase inhibitor may be substituted for the kit phosphatase and protease inhibitors based on ease of use and performance Utilize all other reagents from the kit. Prepare the MSD Tris Lysis buffer by adding 100×HALT protease and phosphatase inhibitor to a 1× final concentration (referred to as MSD complete lysis buffer). Remove tumor samples from the −80° C. freezer and allow to sit at RT to initiate thawing. During the sample thaw, block the pSTAT3 Tyr705 capture plate (cat# K150DID-2) with 150 μL of a blocking solution for a minimum of 1 hr at RT on a plate shaker with vigorous shaking (300-1000 rpm). Seal plates with an adhesive plate seal prior to shaking. Blocking solution should contain the ratio of Blocker A (cat# R93BA-4) 600 mgs: 20 mL of 1×MSD Tris wash buffer (cat# R61TX-2). Once samples begin to thaw, transfer to wet ice to continue thawing. After thawing is completed, carefully mix by pipetting up and down several times using a multichannel pipette. Normalize samples in ice cold MSD complete lysis buffer to a protein concentration of 0.4 μg/μL×100 μL Maintain all normalized tumor samples on ice in a 96 well polypropylene plate until they are added to the pSTAT3 capture plate. After the pSTAT3 capture plate is blocked, wash 4× with 250-300 μL of 1×MSD Tris wash buffer using a Thermo Labsystems Multidrop 384 plate washer. After the final wash, lightly tap to remove any remaining wash buffer. Add a total volume of 25 μL (10 μg) of normalized tumor lysate per well and incubate an additional 2-3 hours at RT on a plate shaker with vigorous shaking (300-1000 rpm). During this incubation, dilute the Sulfo-TAG anti Phospho-STAT 3 detection antibody provided in the kit in the antibody dilution buffer (1 mL of blocking solution combined with 2 mL of 1×MSD Tris wash buffer) by adding 60 μL of Sulfo-TAG anti Phospho-STAT 3 detection antibody to 2.94 mL of antibody dilution buffer. Keep this antibody solution on wet ice until needed. Following tumor lysate incubations, wash the plate 4× with 250-300 μL of 1×MSD Tris wash buffer. After the last wash, tap lightly to remove any remaining wash buffer and add 25 μL/well of the Sulfo-TAG anti Phospho-STAT 3 detection antibody. Incubate the plate an additional 1 hour at RT on a plate shaker with vigorous shaking (300-1000 rpm). During this incubation, dilute the 4×MSD Read Buffer T with surfactant (cat# R92TC-3) to 1× with deionized water and keep at RT. After the detection antibody incubation is complete, wash the plate 4× with 250-300 μL of 1×MSD Tris wash buffer. After the final wash, tap lightly to remove any remaining wash buffer and add a total volume of 150 μl/well of 1×MSD Read Buffer T with surfactant. Read the plate on the Meso Quick Plex SQ 120. Analyze data as indicated below.

Percent pSTAT3 Inhibition Calculation:

Copy and paste raw plate data from the Meso Quick Plex SQ 120 directly into a Microsoft Excel version 2010 worksheet. Organize data into the appropriate format (Dose Response or Time Course). Copy and paste directly into JMP version 11 for pSTAT3 percent inhibition calculations (see formula below).

[1−(Treatment sample Signal/Mean Signal of Vehicle Control)]*100.

Determine a Oneway Anova with treatment group mean compared to vehicle control mean using Dunnett's.

TED Calculations:

The $TED_{50}$ and $TEC_{50}$ values are determined from a dose response study. The $TED_{50}$ is the dose necessary to achieve 50% pSTAT3 inhibition and $TEC_{50}$ is the plasma concentration required to achieve 50% pSTAT3 inhibition, respectively, at two hours.

A compound within the scope of the invention is tested in this assay substantially as described above. The compound of Example 1 shows a $TED_{50}$ of 9 mg/kg and a $TEC_{50}$ of 3.9 μM (n=1). These results show that the compound of Example 1 demonstrates target engagement in rat H1975 IVTI model.

Efficacy Study in HCC827 Xenograft Tumor Model

The purpose of this assay is to measure the ability of compounds to inhibit tumor growth in the HCC827 xenograft mouse model. Grow HCC827 cells (ATCC# CRL-2868, Lot#59392891) according to ATCC specifications at the lowest possible passage number available. Culture cells and maintain in RPMI-1640 supplemented with 10% FBS and incubate at 37° C. in 5% $CO_2$. Harvest cells from flasks using TryPLE, rinse twice in DPBS, resuspend in HBSS, and mix with BD Biosciences basement membrane matrix (MATRIGEL®) to cell suspension to achieve a 1:1 cell/matrix ratio yielding an inoculation volume of 0.2 ml cell/matrix suspension containing $5e^6$ cells. Maintain cell suspensions on ice throughout the inoculation procedure and start implantations within one hour after cell culture harvest. Administer implantations subcutaneously in the right rear flank of female CB17 SCID mice obtained from Harlan (18-20 g). Feed mice Harlan Teklad Protein Extruded 2920X ad libitum and provide water with the rack watering system. Allow the implanted tumor cells to grow as a solid tumor and measure twice a week along with body weight beginning the seventh day after implantation. Determine tumor volumes using the calculation: 0.536*L*W^2. After tumor volume reaches approximately 150-200 $mm^3$, randomize animals and place into groups containing 5-8 animals each. Formulate the compounds in 1% HEC vehicle containing 0.25% Tween 80 and 0.05% antifoam with 1.1 molar equivalent of methanesulfonic acid to form an in situ salt (1.1 mL of 1N methanesulfonic acid per (insert molecular weight) mg of compound). Store test compound at RT. Formulate compounds once per week, and store at RT. Do not add acid to the vehicle control group. Calculate doses based on the most recent group mean body weight. Administer compounds by oral gavage for 28 days either BID or QD depending on dosage.

A compound within the scope of the invention is tested in this assay substantially as described above. The compound of Example 1 shows 31% tumor growth inhibition at 30 mg/kg BID, 22% tumor regression at 60 mg/kg BID, and 22% tumor regression at 120 mg/kg QD. These results show that the compound of Example 1 demonstrates tumor regression in the HCC827 xenograft tumor model.

I claim:

1. A compound of Formula I:

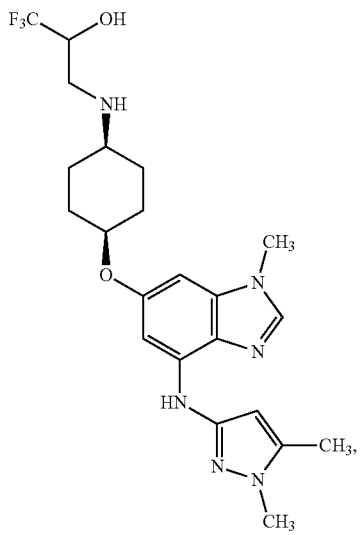 [SMILES: Cc1cc(Nc2cc(O[C@H]3CC[C@@H](NC[C@@H](O)C(F)(F)F)CC3)cc3c2ncn3C)nn1C]

Formula I or a pharmaceutically acceptable salt thereof.

2. The compound according to claim 1 wherein the compound is selected from the group consisting of:

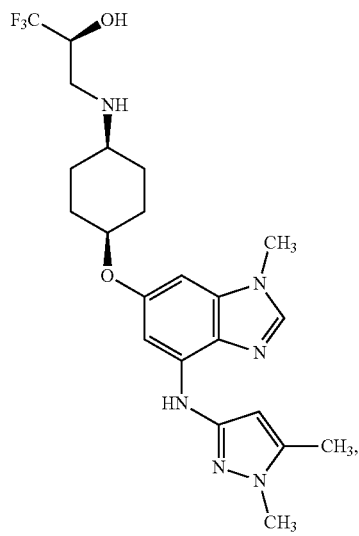 [SMILES: Cc1cc(Nc2cc(O[C@H]3CC[C@@H](NC[C@H](O)C(F)(F)F)CC3)cc3c2ncn3C)nn1C]

or a pharmaceutically acceptable salt thereof, and

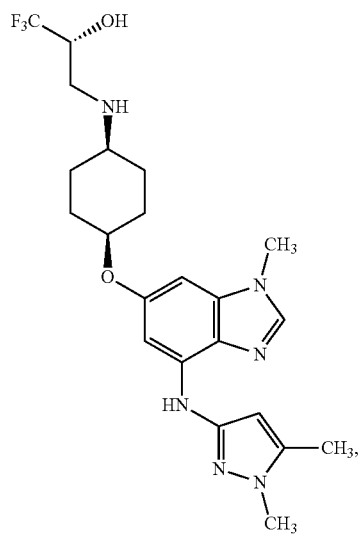

or a pharmaceutically acceptable salt thereof.

3. The compound according to claim 2 which is

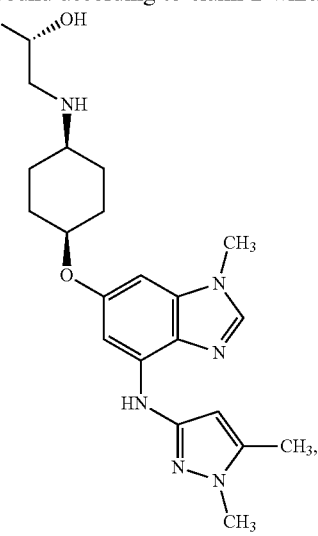

or a pharmaceutically acceptable salt thereof.

4. The compound according to claim 2 which is

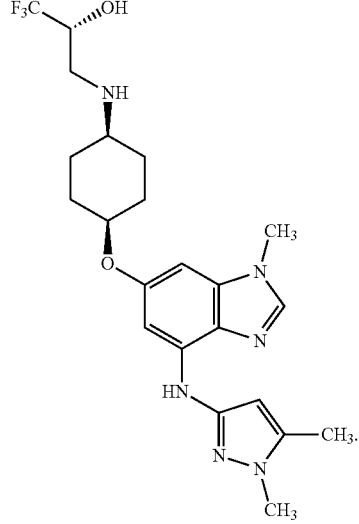 [SMILES: Cc1cc(Nc2cc(O[C@H]3CC[C@@H](NC[C@@H](O)C(F)(F)F)CC3)cc3c2ncn3C)nn1C]

5. A pharmaceutical composition comprising a compound of Formula I:

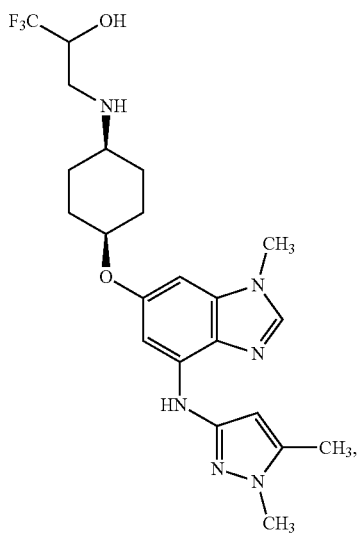 [SMILES: Cc1cc(Nc2cc(O[C@H]3CC[C@@H](NC[C@@H](O)C(F)(F)F)CC3)cc3c2ncn3C)nn1C]

Formula I or a pharmaceutically acceptable salt thereof, and a pharmaceutically acceptable carrier, diluent, or excipient.

6. The pharmaceutical composition according to claim 5 wherein the compound is selected from the group consisting of:

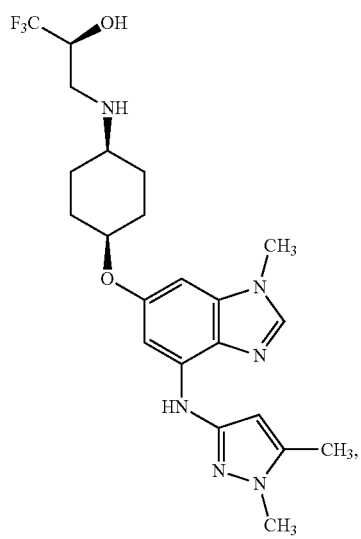 [SMILES: Cc1cc(Nc2cc(O[C@H]3CC[C@@H](NC[C@H](O)C(F)(F)F)CC3)cc3c2ncn3C)nn1C]

or a pharmaceutically acceptable salt thereof, and

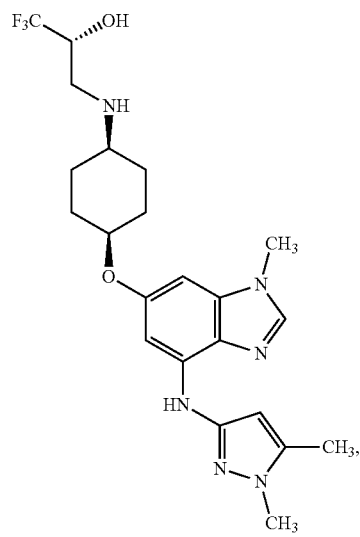

or a pharmaceutically acceptable salt thereof.

7. The pharmaceutical composition according to claim 6 wherein the compound is

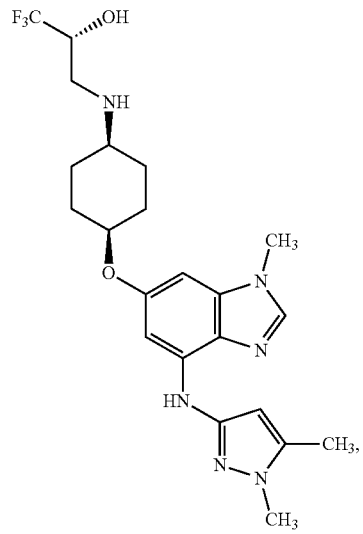

or a pharmaceutically acceptable salt thereof.

8. The pharmaceutical composition according to claim 6 wherein the compound is

10. The method according to claim 9, wherein the compound is selected from the group consisting of:

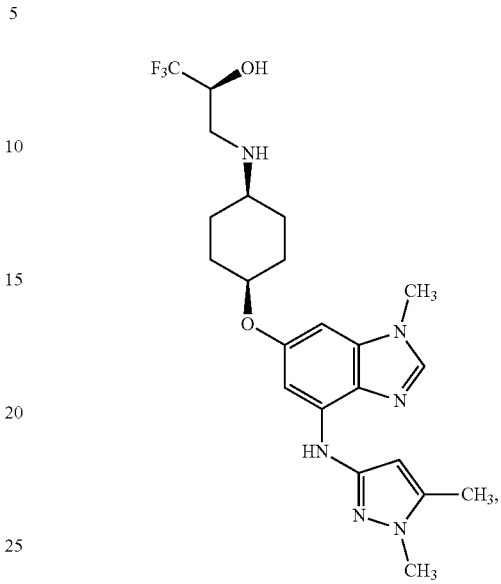

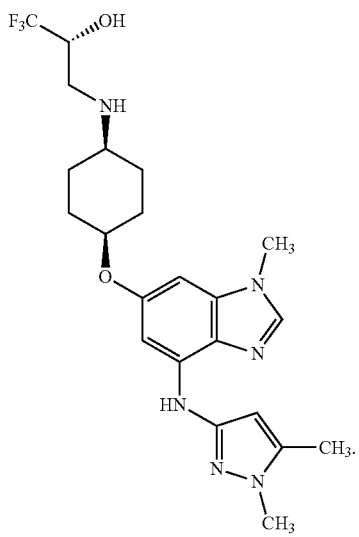 [SMILES: Cc1cc(Nc2cc(O[C@H]3CC[C@@H](NC[C@@H](O)C(F)(F)F)CC3)cc3c2ncn3C)nn1C]

9. A method of treating cancer, comprising administering to a patient in need thereof, an effective amount of a compound of Formula I:

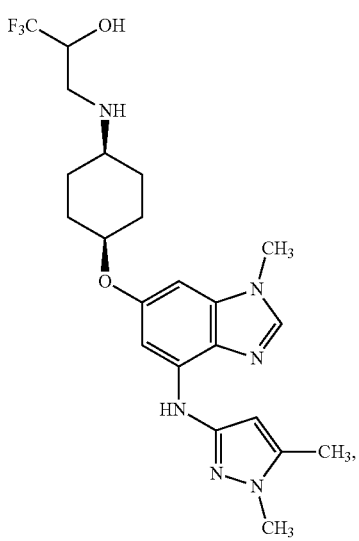 [SMILES: Cc1cc(Nc2cc(O[C@H]3CC[C@@H](NC[C@@H](O)C(F)(F)F)CC3)cc3c2ncn3C)nn1C]

Formula I or a pharmaceutically acceptable salt thereof, and

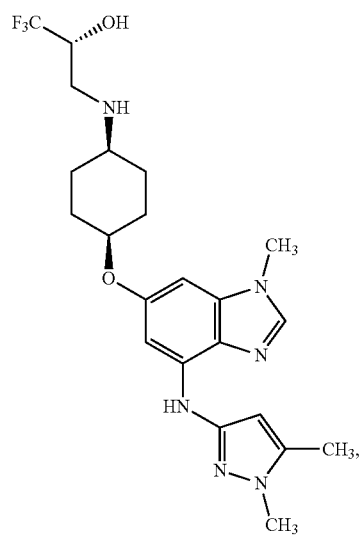

or a pharmaceutically acceptable salt thereof.

11. The method according to claim 10 wherein the compound is or a pharmaceutically acceptable salt thereof, wherein the cancer is selected from the group consisting of lung cancer, including non-small cell lung cancer and lung adenocarcinoma, adenocarcinoma, hepatocellular carcinoma, including Asian hepatocellular carcinoma, colorectal cancer, breast cancer, and leukemia, including acute lymphocyte leukemia.

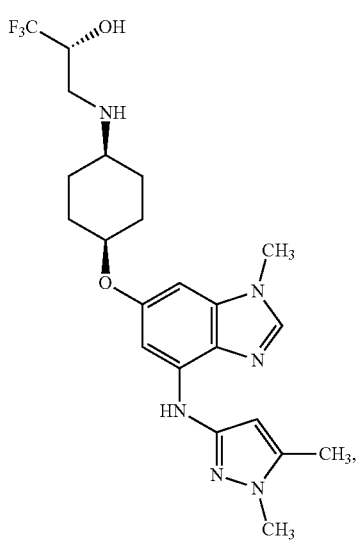

or a pharmaceutically acceptable salt thereof.

12. The method according to claim 10 wherein the compound is

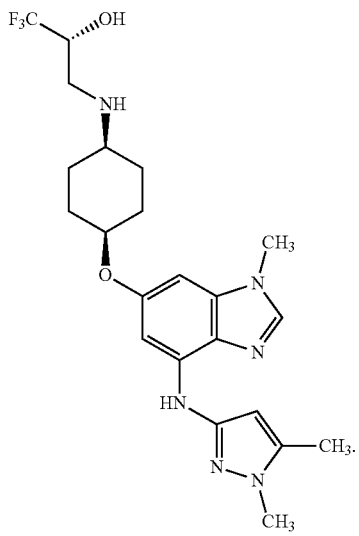 [SMILES: Cc1cc(Nc2cc(O[C@H]3CC[C@@H](NC[C@@H](O)C(F)(F)F)CC3)cc3c2ncn3C)nn1C]

13. The method according to claim 9, wherein the cancer is non-small cell lung cancer.

14. The method according to claim 9, wherein the cancer is lung adenocarcinoma.

15. The method according to claim 9, wherein the cancer is breast cancer.

16. The method according to claim 9, wherein the cancer is Asian hepatocellular carcinoma.

17. The method according to claim 10, wherein the cancer is non-small cell lung cancer.

18. The method according to claim 10, wherein the cancer is lung adenocarcinoma.

19. The method according to claim 10, wherein the cancer is breast cancer.

20. The method according to claim 10, wherein the cancer is Asian hepatocellular carcinoma.

21. The method according to claim 11, wherein the cancer is non-small cell lung cancer.

22. The method according to claim 11, wherein the cancer is lung adenocarcinoma.

23. The method according to claim 11, wherein the cancer is breast cancer.

24. The method according to claim 11, wherein the cancer is Asian hepatocellular carcinoma.

25. The method according to claim 12, wherein the cancer is non-small cell lung cancer.

26. The method according to claim 12, wherein the cancer is lung adenocarcinoma.

27. The method according to claim 12, wherein the cancer is breast cancer.

28. The method according to claim 12, wherein the cancer is Asian hepatocellular carcinoma.

* * * * *